United States Patent [19]

Brock

[11] Patent Number: 4,663,157

[45] Date of Patent: May 5, 1987

[54] SUNSCREEN COMPOSITIONS

[75] Inventor: Earl D. Brock, Burlington, Ky.

[73] Assignee: The Proctor & Gamble Company, Cincinnati, Ohio

[21] Appl. No.: 781,084

[22] Filed: Sep. 26, 1985

Related U.S. Application Data

[63] Continuation-in-part of Ser. No. 706,701, Feb. 28, 1985, abandoned.

[51] Int. Cl.$^4$ .......................... A61K 7/42; A61K 7/44; A61K 9/10
[52] U.S. Cl. ......................................... 424/59; 424/60; 424/78; 424/81; 514/773; 514/781; 514/783; 514/938; 514/949
[58] Field of Search ........................ 424/59, 60, 78, 81

[56] References Cited

U.S. PATENT DOCUMENTS

| | | | |
|---|---|---|---|
| 3,755,560 | 8/1973 | Dickert et al. | 424/59 |
| 3,784,488 | 1/1974 | Steinhauer et al. | 524/566 |
| 3,821,363 | 6/1974 | Black et al. | 424/59 |
| 3,895,104 | 7/1975 | Karg | 424/81 |
| 3,980,617 | 9/1976 | Jacquet et al. | 260/47 UA |
| 4,057,622 | 11/1977 | Hase et al. | 514/939 |
| 4,166,109 | 8/1979 | Jacquet et al. | 424/59 |
| 4,172,122 | 10/1979 | Kubik et al. | 424/60 |
| 4,233,430 | 11/1980 | Jacquet et al. | 526/259 |
| 4,384,974 | 5/1983 | Guthauser | 424/59 |
| 4,504,644 | 3/1985 | Lang | 424/60 |
| 4,522,808 | 6/1985 | Jacquet et al. | 424/81 |
| 4,524,061 | 6/1985 | Cho et al. | 424/81 |

FOREIGN PATENT DOCUMENTS

| | | | |
|---|---|---|---|
| 571216 | 2/1959 | Canada | 424/60 |
| 2,654,925 | 6/1977 | Fed. Rep. of Germany | 424/60 |
| 8114552 | 1/1983 | France | 424/59 |
| 7309147 | 12/1974 | Netherlands | 424/59 |
| 957175 | 5/1964 | United Kingdom | 424/81 |
| 1407670 | 9/1975 | United Kingdom | 424/59 |
| 1465190 | 2/1977 | United Kingdom | 424/59 |
| 1557580 | 12/1979 | United Kingdom | 424/59 |
| 2028131 | 3/1980 | United Kingdom | 424/59 |

*Primary Examiner*—Dale R. Ore
*Attorney, Agent, or Firm*—Richard C. Witte; John V. Gorman; Douglas C. Mohl

[57] ABSTRACT

Sunscreen compositions are disclosed which are resistant to rub-off and the concomitant loss of protection provided by the sunscreen.

14 Claims, No Drawings

SUNSCREEN COMPOSITIONS

CROSS REFERENCE TO RELATED APPLICATION

This application is a continuation-in-part application of my co-pending application having Ser. No. 706,701, filed on Feb. 28, 1985, now abandoned.

TECHNICAL FIELD

The present invention relates to novel skin protection compositions which have improved resistance to rub-off of the sunscreen agent(s).

BACKGROUND OF THE INVENTION

The damaging effects of sunlight on skin are well documented. In spite of this, people are forced to be in the sun for long periods of time due to their occupation. Others are in the sun for long periods due to their leisure time activities and/or a desire to have a tanned appearance.

To protect skin from the damaging effects of the sun's rays, sunscreening compositions have been developed which absorb ultraviolet light in the erythemal region. Many of these developments have attempted to improve the substantivity of the sunscreen agent, particularly improving the resistance to being washed off by water. Examples of such compositions are disclosed in U.S. Pat. No. 3,784,488, Jan. 8, 1974 to Steinhauer et al. disclosing organic soluble polymers to form a continuous film on the skin. The polymers are insoluble in the sunscreen agent. Other references disclosing sunscreen compositions containing polymeric materials include U.S. Pat. No. 3,821,363, June 28, 1974 to Black et al. and U.S. Pat. No. 3,895,104, July 15, 1975 to Karg. These compositions all form continuous films with the object being to trap the sunscreen agent on the skin.

Another approach to formulating substantive sunscreen compositions is to use oil soluble polymers along with the sunscreen agent. The polymer does not form a continuous polymeric film but rather, being dissolved in the sunscreen, helps to bind the sunscreen to the skin. One such approach is disclosed in U.S. Pat. No. 4,172,122, Oct. 23, 1979 to Kubik et al. This, as well as the previously described patents, are incorporated herein by reference.

While the prior art suggests numerous methods for improving the performance of sunscreen compositions, there still exists the need for more improvements. One area of desired improvement is in the resistance exhibited by the compositions to being rubbed off. The present inventor has discovered that maintaining the ratio of sunscreen agent to polymer within a certain range provides for improved product rub-off while still maintaining pleasing aesthetics. The polymers used are soluble in the oily, sunscreen material and other oil materials.

In view of the above, it is an object of the present invention to provide effective sunscreen compositions.

It is a further object of the present invention to provide compositions which are resistant to rub-off.

It is still a further object of the present invention to provide sunscreen compositions which have good cosmetic properties (e.g., feel, rub-in, lack of excessive greasiness and/or stickiness, etc.).

These and other objects will become readily apparent from the detailed description which follows.

Unless otherwise indicated, all percentages and ratios herein are by weight.

SUMMARY OF THE INVENTION

The present invention relates to oil in water emulsion sunscreen compositions comprising from about 1% to about 20% of a sunscreen or mixture of sunscreens, from about 0.25% to about 3% of a copolymer of ethylene and acrylic acid, from about 2% to about 10% of an emulsifier and from about 70% to about 96% of water. The ratio of sunscreen:polymer in the compositions is from about 12:1 to about 15:1. The essential as well as optional components are described in detail below.

DETAILED DESCRIPTION

Essential Components

Sunscreen Agent

The term "sunscreen agent" as used herein includes the specific compounds ethylhexyl p-methoxycinnamate and butyl methoxydibenzoylmethane and mixtures thereof. The former compound is a UVB absorber while the latter absorbs UV rays in the A range. Other sunscreens useful in the present compositions are 2-hydroxy-4-methoxybenzophenone and octyl dimethyl p-aminobenzoic acid. Mixtures of these are also acceptable as are mixtures with the previously mentioned sunscreens. Still other sunscreens are digalloyl trioleate, 2,2-dihydroxy-4-methoxy benzophenone, ethyl 4-[bis(-hydroxypropyl)]aminobenzoate, 2-ethylhexyl 2-cyano-3,3-diphenylacrylate, ethyl hexyl p-methoxy cinnamate, 2-ethylhexyl salicylate, glyceryl p-aminobenzoate, 3,3,5-trimethylcyclohexyl salicylate, methyl anthranilate, p-dimethyl aminobenzoate and 2-ethylhexyl p-dimethyl amino benzoate. Mixtures of these latter compounds may also be used. These compounds do not penetrate the skin and are therefore benefited to a greater extent by the improved resistance to rub-off than would compositions which do penetrate the skin.

The amount of the compounds useful in the compositions of the present invention is from about 1% to about 20%, preferably from about 7% to about 12%.

Polymer

The polymer useful in the present composition is a copolymer of ethylene and acrylic acid. These monomers:

Ethylene  $CH_2=CH_2$

Acrylic acid 

are present in polymeric form as follows:

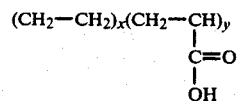

wherein the ratio of x:y is from about 1:24 to about 1:9. The weight average molecular weight is from about 3500 to about 4500, preferably from about 4000 to about 4300.

Emulsifier

Emulsifiers suitable for use in the present invention can be any of a wide variety disclosed in the prior patents and other references. Two patents, incorporated by reference herein, which disclose suitable emulsifiers are U.S. Pat. No. 3,755,560, Aug. 28, 1973 to Dickert et al. and U.S. Pat. No. 4,421,769, Dec. 20, 1983 to Dixon et al. Preferred emulsifiers are anionic or nonionic although other types may also be used. Another reference disclosing an extensive number of emulsifiers is McCutcheon's *Detergents and Emulsifiers*. North American Edition, 1983, incorporated herein by reference.

Suitable emulsifier types include ethoxylated fatty acids, ethoxylated esters, ethoxylated ethers, ethoxylated alcohols, phosphated esters, polyoxyethylene fatty ether phosphates, fatty acid amides, acyl lactylates, soaps and mixtures thereof. Fatty alcohols such as cetyl and stearyl alcohol and cetearyl alcohol are also regarded as emulsifiers for purposes of the present invention.

Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoyl-2-lactylate and calcium stearoyl-2-lactylate. Soaps are also acceptable emulsifiers. The soaps may be formed in situ in processing the composition and are preferably alkali metal or triethanolamine salts of long chain fatty acids. Such soaps include sodium stearate, triethanolamine stearate and the similar salts of lanolin fatty acids.

The emulsifier, or mixture of emulsifiers, is present at a level of from about 2% to about 10%, preferably from about 2.5% to about 5%.

Water

Water is the last of the essential components of the present compositions and is generally present at a level of from about 70% to about 96%, preferably from about 75% to about 85%.

Optional Components

The compositions of the present invention may contain in addition to the aforementioned essential components a wide variety of additional oil soluble materials and water soluble materials.

Among the optional oil soluble materials are nonvolatile silicone fluids such as polydimethyl siloxanes with viscosities ranging from about 10 to about 100,000 centistokes at 25° C. These siloxanes are available from Dow Corning Corporation as the Dow Corning 200 series.

Other oil soluble materials include fatty alcohols such as cetyl alcohol and stearyl alcohol; esters such as cetearyl palmitate, lauryl myristate and isopropyl palmitate; oils such as castor oil, jojoba oil, cottonseed oil, peanut oil and sesame oil; waxes such as petrolatum, cersin wax, carnauba wax, beeswax, and castor wax; lanolin, its derivatives and components such as acetylated lanolin, lanolin alcohols and lanolin fatty acids. Sterols such as cholesterol and phytosterol are also useful herein.

These optional oil phase materials may individually comprise up to about 20% of the total composition, preferably up to about 10%.

Additional water soluble materials may also be present in the compositions of this invention. Included are humectants such as glycerin, sorbitol, propylene glycol, alkoxylated glucose and hexanetriol; tyrosine; thickening agents such as carboxyvinyl polymers (Carbopols-$^R$—offered by B. F. Goodrich Company, such polymers are described in detail in U.S. Pat. No. 2,798,053, July 2, 1957 to Brown, incorporated herein by reference); ethyl cellulose, polyvinyl alcohol, carboxymethyl cellulose, vegetable gums and clays such as Veegum ® (magnesium aluminum silicate, R. T. Vanderbilt, Inc.); proteins and polypeptides; preservatives such as the methyl, ethyl, propyl and butyl esters of hydroxybenzoic acid (Parabens—Mallinckrodt Chemical Corporation), EDTA, methylisothiazolinone and imidazolidinyl ureas (Germall 115—Sutton Laboratories); and an alkaline agent such as sodium hydroxide or potassium hydroxide to neutralize, if desired, part of the fatty acids or thickener which may be present.

The optional water phase materials may individually comprise up to about 20% of the total composition, preferably up to about 10%.

The present compositions may also contain agents suitable for aesthetic purposes such as perfumes and dyes.

The pH of the compositions herein is preferably in the range of from about 4.5 to about 9.

It is preferred that the mean particle size of the dispersed oil phase materials (e.g., sunscreen, polymer, perfumes, etc.) dispersed in the aqueous phase be in the range of from about 5 to about 10 microns with greater than 75% of the particles being less than 12 microns.

METHOD OF MANUFACTURE

The compositions of the present invention can be prepared using the method described in the Examples.

INDUSTRIAL APPLICABILITY

The compositions described herein are particularly suited for protecting the skin of the body, particularly the face. An effective amount, from about 0.5 mg/cm$^2$ skin to about 5 mg/cm$^2$ skin, is used and rubbed into the skin.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I-VII

The following example compositions are representative of the present invention.

| Component | Weight % | | | | | | |
| --- | --- | --- | --- | --- | --- | --- | --- |
| | I | II | III | IV | V | VI | VII |
| Ethylhexyl p-methoxycinnamate | 6.00 | 2.0 | 3.5 | 4.5 | 7.0 | 7.5 | 4.9 |
| Butyl Methoxydibenzoylmethane | 4.00 | 1.0 | 2.5 | 3.0 | 3.0 | 10.0 | 2.1 |
| Ethylene/Acrylate Copolymer[1] | .75 | 0.25 | 0.45 | 0.55 | 0.75 | 1.25 | 0.5 |
| Glycerin | 3.50 | 6.00 | 5.50 | 4.00 | 3.50 | 2.00 | 5.0 |

-continued

| Component | Weight % | | | | | | |
|---|---|---|---|---|---|---|---|
| | I | II | III | IV | V | VI | VII |
| Petrolatum | 1.50 | 2.50 | 2.00 | — | 1.50 | 0.50 | 2.0 |
| Dimethicone[2] | .30 | 0.50 | 0.30 | 0.40 | 0.30 | 0.20 | 0.40 |
| Steareth-100 | .48 | 0.48 | 0.7 | 0.5 | 0.375 | 0.90 | 0.70 |
| Glycerol Monostearate | .32 | 0.32 | 0.8 | 0.5 | 0.875 | 0.80 | 0.30 |
| Cetyl Alcohol | 1.20 | 1.2 | 1.0 | 1.0 | 1.0 | 1.50 | 1.20 |
| Stearic Acid | .52 | .52 | .52 | 0.52 | 0.52 | 0.52 | 0.52 |
| Carbomer 934[3] | .08 | .08 | .15 | 0.15 | 0.18 | 0.20 | 0.10 |
| Carbomer 941[3] | .06 | .06 | .08 | 0.08 | 0.05 | 0.05 | 0.10 |
| Methyl Paraben[4] | .20 | .2 | .2 | .2 | 0.20 | .2 | 0.20 |
| Propyl Paraben | .10 | .1 | .1 | .1 | 0.10 | .1 | 0.10 |
| Imidazolidinyl Urea | .10 | .1 | .1 | .1 | .10 | .1 | 0.10 |
| Tetrasodium EDTA | .10 | .1 | .1 | .1 | .10 | .1 | 0.10 |
| Tyrosine | .10 | .1 | .1 | .1 | .10 | .1 | 0.10 |
| Potassium Hydroxide | .31 | 0.35 | 0.37 | 0.35 | 0.395 | 0.32 | 0.37 |
| Titanium Dioxide | .30 | 0.20 | 0.30 | 0.30 | 0.40 | 0.50 | 0.40 |
| Perfume | .18 | 0.08 | 0.15 | 0.18 | 0.10 | 0.25 | 0.15 |
| Water | 79.90 | 83.86 | 81.08 | 83.37 | 79.455 | 72.91 | 80.66 |
| TOTAL | 100.00 | 100.00 | 100.00 | 100.00 | 100.00 | 100.00 | 100.00 |

[1]Offered by Allied Chemical Company as AC 540A having a weight average molecular weight of 4271 and having 5% ethylene
[2]Polydimethylsiloxane offered by Dow Corning as DC-200
[3]Carboxyvinyl polymers offered by B. F. Goodrich
[4]Preservatives offered by Sutton Laboratories The above compositions can be made by adding the following components as described:

| Part | Material |
|---|---|
| I | Water |
| | Carbomer 934 |
| | Carbomer 941 |
| | Methyl Paraben |
| | Propyl Paraben |
| | Glycerine |
| II | Ethylhexyl p-methoxycinnamate |
| | Butyl Methoxydibenzoylmethane |
| | Cetyl Alcohol |
| | Glyceryl Stearate |
| | Steareth-100 |
| | Stearic Acid |
| | Dimethicone |
| | Petrolatum |
| | Ethylene/Acrylate Copolymer |
| III | Tetrasodium EDTA |
| | Potassium Hydroxide |
| | Titanium Dioxide |
| IV | Tyrosine |
| | Imidazolidinyl Urea |
| | Perfume |

The composition is made by mixing the water phase (Part I) materials at 71°-99° C. in a scale-mounted mix tank fitted with baffles and an agitator. The oil phase (Part II) is mixed at 71°-110° C. in a separate mix tank fitted with an agitator. Both Part I and Part II are mixed until homogeneous phases are obtained.

The water phase (Part I) is then pumped into the oil phase (Part II) in an amount equal to 60-110% of the oil phase (Part II). This oil/water premix is held at a temperature of from about 71°-99° C. and agitated until a homogeneous mixture is obtained. The oil/water premix is then pumped into the remaining water phase (Part I) and held at a temperature of from about 71°-99° C. Part III ingredients are then added while maintaining agitation and holding the temperature at 71°-99° C. The composition is then passed through a closed vessel equipped with an ultrasonic probe at the flow rate of 0.5-6.5 kg/min. The ultrasonic frequency may range from 15 to 40 kHz. The composition is further processed through a heat exchanger and/or jacket cooling at a temperature of 71°-99° C. The part IV components are then added while maintaining agitation until a homogeneous mixture is obtained.

The composition is then pumped through a heat exchanger to cool to 21°-32° C. While waiting to reach steady-state operation, the composition may be recirculated back to the mix tank. The composition is then packed into glass bottles.

The compositions are all easy to apply, exhibit improved rub-off resistance and provide protection to the area of the skin treated.

EXAMPLE VIII

A composition identical with Example I except that the ethylene/acrylate copolymer level was 0.5% was prepared.

The compositions were tested on panelists using the following procedure. Each panelist does the following:
1. Washes her face with soap and water.
2. Dries her face with paper towel.
3. Wipes her face with cotton wetted with ethanol.
4. Applies 200 mg of the first composition on one side of the face and 200 mg of the second composition to the other side.
5. Waits 5 minutes after product application.
6. Extracts a 1.5 cm$^2$ circular area on left side with ethanol (3.5 ml) using a tygon tubing as follows: (a) the tygon tubing is pressed on the cheek and 3.5 mls alcohol is placed inside the tubing, (b) after 1.5 minutes the alcohol is removed and transferred into a 10 ml volumetric flask, (c) a and b are repeated, (d) the extract from c is added to the same 10 ml volumetric flask as the extract from b, (e) a through d are repeated using the other cheek and a different volumetric flask.
7. After 4 hours, repeats the extraction procedure 6a through 6e.
8. Each volumetric flask is then filled to capacity with ethanol.

9. The absorbance of the extracted solutions are read using a UV spectrophotometer, the instrument having been calibrated using the absorbance of standard sunscreen solutions.

10. The percentage of sunscreen recovered is then determined by taking the ratio of absorbance from the extraction at 4 hours and the extraction at 5 minutes.

In the comparison of Example I with the composition with only 0.5% of the ethylene/acrylate copolymer, Example I retained 56% of the sunscreen applied while the 0.5% polymer product only retained 43%.

What is claimed is:

1. An oil in water emulsion sunscreen composition comprising:
   (A) from about 1% to about 20% of an oil soluble sunscreen;
   (B) from about 0.25% to about 3% of an ethylene acrylic acid copolymer having the formula

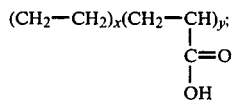

(C) from about 2% to about 10% of an emulsifier; and
   (D) from about 70% to about 96% of water;
wherein the ratio of A:B is from about 12:1 to about 15:1 and the ratio of x:y is from about 1:9 to about 1:24 and the molecular weight of B is from about 3500 to about 4500.

2. A composition according to claim 1 which also contains a humectant.

3. A composition according to claim 1 which also contains a thickening agent.

4. A composition according to claim 1 wherein the sunscreen is selected from the group consisting of 2-ethylhexyl p-methoxycinnamate, butyl methoxydibenzoylmethane, 2-hydroxy-4-methoxy-benzophenone, octyl dimethyl p-aminobenzoic acid and mixtures thereof.

5. A composition according to claim 1 wherein the emulsifier is a mixture of anionic and nonionic emulsifiers.

6. A composition according to claim 3 wherein the humectant is glycerine.

7. A composition according to claim 6 which also contains a thickener.

8. A composition according to claim 7 wherein the thickener is a carboxyvinyl polymer.

9. A composition according to claim 8 which in addition contains petrolatum.

10. A composition according to claim 1 wherein the oil phase particles have a mean particle size of from about 5 to about 10 microns.

11. A method of protecting skin from UV rays comprising the following steps to be performed prior to UV exposure:
   (A) applying from about 0.5 mg/cm$^2$ to about 5 mg/cm$^2$ of a composition according to claim 1 to the skin area desired to be protected; and
   (B) rubbing the composition into the skin.

12. A method according to claim 11 wherein the composition is according to claim 5.

13. A method according to claim 11 wherein the composition is in accordance with claim 8.

14. A method according to claim 11 wherein the composition is in accordance with claim 9.